United States Patent [19]

Kaiho et al.

[11] Patent Number: 4,507,309

[45] Date of Patent: Mar. 26, 1985

[54] PHARMACEUTICAL COMPOSITION FOR TREATING TRANSPLANTED TUMOR CELLS

[75] Inventors: Shin-ichi Kaiho, Chiba; Koji Mizuno, Saitama; Shun-ichi Hata, Kanagawa; Masuo Koizumi, Tokyo; Masamitsu Honda, Tokyo; Yasushi Murakami, Tokyo; Shigeru Takanashi, Saitama; Minoru Shindo, Tokyo, all of Japan

[73] Assignee: Chugai Seiyaku Kabushiki Kaisha, Tokyo, Japan

[21] Appl. No.: 367,354

[22] Filed: Apr. 12, 1982

[30] Foreign Application Priority Data

Apr. 21, 1981 [JP] Japan .................. 56-59153

[51] Int. Cl.³ ............................. A61K 31/42
[52] U.S. Cl. ........................... 514/379
[58] Field of Search ..................... 424/272

[56] References Cited

PUBLICATIONS

Davis R. B. et al., "Condensation of Aromatic Nitro Compounds with Acrylacetonitriles. II. Some p-Substituted Nitrobenzenes", *J. Org. Chem.*, 25, 1884–88, (1960).

Tanasescu, I. et al., "Sur les Acridones (XIX), Syntheses et Comportements de Certaines Bromoacridones Substituees", *Bull. Chim. France*, 693–96, (1960).

Tanasescu, I. et al., "Sur les Acridones (X) (1) p.Chlorophenylanthranile et Chloro-3-Acridone", *Bull. Chim. France*, 3, 2383–85, (1936).

Tanasescu, I. et al., "Sur la Condensation des o-Nitrobenzaldehydes Avec l'Aniline (III) (1). Comportement Photophimique des Anthraniles et Triphenylmethanes Obtenus", *Bull. Chim. France*, 4, 245–258, (1937).

Guyot, A. et al., "Sur le Produit de la Combinaison de l'Aldehyde Ortho-Nitrobenzoique Avec le Phenol en Presence d'Acide Chlorhydrique", *Bull. Chim. France*, 31, 530–533, (1904).

Simpson, J. C. E. et al., "58. Cinnolines. Part I. Some New Examples", *J. Chem. Soc.*, 353–58, (1942).

Leiter et al., Cancer Research, Part 2, vol. 24, No. 6, Jul. 1964, pp. 880–887, 891, 895 and 1034, (No. 56311).

*Primary Examiner*—Jerome D. Goldberg
*Attorney, Agent, or Firm*—Browdy and Neimark

[57] ABSTRACT

A treating agent whose effective ingredient is an anthranyl derivative of the formula:

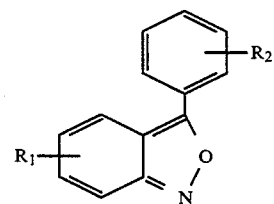

(wherein $R_1$ and $R_2$ may be the same or different and represent a hydrogen atom, a hydroxyl group, a lower alkoxy group, preferably $C_1$–$C_3$ alkoxy group, a lower alkyl group, preferably $C_1$–$C_3$ alkyl group, a nitro group or a halogen atom) is disclosed.

5 Claims, No Drawings

PHARMACEUTICAL COMPOSITION FOR TREATING TRANSPLANTED TUMOR CELLS

FIELD OF THE INVENTION

The present invention relates to a treating agent the effective ingredient of which is an anthranyl derivative of the formula:

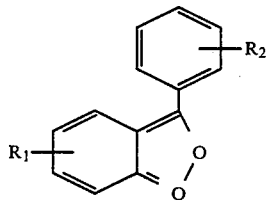

(I)

wherein $R_1$ and $R_2$ may be the same or different and represent a hydrogen atom, a hydroxyl group, a lower alkoxy group, preferably $C_1$–$C_3$ alkoxy group, a lower alkyl group, preferably $C_1$–$C_3$ alkyl group, a nitro group or a halogen atom.

BACKGROUND OF THE INVENTION

Conventional chemotherapeutic agents commonly used in treatments against some cancers include alkylating agents such as nitrogen mustards and ethyleneimines; metabolic antagonists such as folic acid antagonist, purine antagonist and pyrimidine antagonist; antibiotics such as actinomycin C and mitomycin C; pituitary adrenal hormone; and alkaloids. These compounds inhibit the growth of some cancer cells by interfering with any of the biological phenomena from DNA to protein synthesis and have direct killing effect on the cells. But the killing effect of these compounds is not selective and affects not only the cancer cells but also normal cells. Therefore, the toxicity of these compounds is unjustifiably greater than their expected effect.

As a result of studies for a compound that has selective effect against transplanted cancer cells, the present inventors have found unexpectedly that anthranyl derivatives of the formula (I) act only on transplanted cancer cells to inhibit their growth or eliminate them. The present invention has been accomplished on the basis of this fact. The mechanism of the peculiar effect of the anthranyl derivatives of (I) is not altogether clear, but presumably they redifferentiate the abnormal cells which are the product of abnormal differentiation of normal cells.

The anthranyl derivatives that can be used in the present invention have the following formula and are listed in Table 1. It is to be understood that the compounds that can be used in the present invention are by no means limited to these derivatives.

TABLE 1

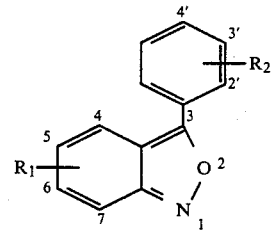

| Compound No. | $R_1$ | $R_2$ | Melting point (°C.) |
|---|---|---|---|
| 1 | 5-Cl | H | 114–115 |
| 2 | 5-Br | H | 117–118 |
| 3 | 6-$NO_2$ | 4'-$CH_3$ | 210–211 |
| 4 | H | 4'-Cl | 156–157 |
| 5 | 5-Cl | 4'-Cl | 214–215 |
| 6 | 5-Br | 4'-Cl | 213–214 |
| 7 | 5-Cl | 4'-OH | 240–241 |
| 8 | 5-Cl | 4'-$OCH_3$ | 144–145 |
| 9 | 5-Br | 4'-$OCH_3$ | 134–135 |

The above named compounds are known: compounds 1, 2, 6 and 9 are described in J.O.C., 25, 1884 (1960), compound 3 in Bull. Soc. Chim. France, 693 (1960), compound 4 in supra (5) 3, 2383 (1936), compound 5 in supra (5) 4, 245 (1937), compound 8 in supra (3) 31, 530 (1904), and compound 7 in J.C.S. 353 (1942). But none of these references teach or suggest the use of the respective compounds for therapeutic purposes.

The treating agents of the present invention can be administered either orally or parenterally in the form of an intramuscular injection, subcutaneous injection, intravenous injection or suppository. The agents can be formulated in a desired preparation such as a tablet, slow release agent, powder, capsule, suspension, injection or suppository by a conventional technique. For instance, they can be formulated in a tablet, granule or powder by mixing with a pharmaceutical carrier (e.g. excipient, binder or solvent) such as lactose, starch, mannitol, saccharose, kaolin, crystalline cellulose, talc, calcium, carbonate, magnesium stearate, calcium stearate or hydrogenpotassium phosphate; or they may be formulated in a capsule by filling a hard capsule with granules or powder or filling a soft capsule with a solution in oil; or they may be formulated in a suspension by suspending gum arabic powder or saccharose in an aqueous solution of them and controlling the pH of the suspension; or they may be formulated in an injection by mixing with mannitol. The effective ingredient of the present invention is used in an amount of 10–70 wt% on the basis of the specific form of preparation in which it is administered. The dose varies with the type of abnormal cell to be treated, its severity, and the method of administration, and is usually from 10 mg to 3 g per day.

EXAMPLE 1

(1) Preparation of cell suspensions

Mouse Cloudman S91 melanoma cells (M-3) were suspended in a Ham's F-12 medium containing 15% horse serum and 2.5% fatal bovine serum. The suspension was put in a plastic culture flask and incubated in a $CO_2$ incubator (5% $CO_2$, 95% air) at 37° C. for 10 days. The supernatant was decanted, and a 0.05% trypsin solution was added to the remaining culture that contained the grown cells adhering to the bottom of the flask. Two or three minutes later, the trypsin solution was removed, and a prewarmed culture medium was added to rinse the adherent cells and form a liquor in which the cells were suspended.

(2) Cell culture and addition of test compounds

The cells prepared in (1) were plated at $2 \times 10^5$ cells in plastic Petri dishes (35 mm in dia.) and each dish was incubated in a $CO_2$ incubator at 37° C. Forty eight hours after plating, the medium was removed, and 2 ml of the medium used in (1) above containing one of the test compounds was added, and the mixture was incubated further. The medium was changed every 48 hours.

(3) The growth of cells

The growth of the cells under incubation was checked every other day. Each plastic Petri dish was removed from the incubator and the medium was removed. One ml of 0.05% trypsin solution was added, the cells were suspended in this solution by pipetting and the number of cells was counted with a hemocytometer. The effectiveness of the test compounds was evaluated by the following criteria: little increase in the cell count was observed the day after the addition of the test compound onward (+++), the cell count increased the day after the addition of the test compound onward, but the growth rate was apparently reduced (++), there was no difference from the control for the period of several days from the addition of the test compound, but thereafter, the growth rate for the treated group became apparently lower than that for the control (+); at no time was the growth rate inhibited in comparison with that for the control (−).

(4) Morphological changes

A microscopic observation of the cells was made 4 days after the addition of the specific test compound. The indices for the morphological changes were the number of dendrite-like-structure cells and the ratio of the size of the nucleus to that of the cell. The change was indicated as (+) when the value of each index was 2 to 3 times as large as that for the control, and (++) when the value was at least 4 times as great.

(5) Melanine production

The cells were harvested on the 10th day of the incubation, and the melanine content was measured by the method of Whittaker (Dev. Biol., 8, 99, 1963). The melanine content was determined as the weight of melanine per mg of protein measured by the method of Lowry et al., and the percent increase in the melanine content was calculated by the following formula:

Percent increase in the melanine content =

$$\left( \frac{\text{melanine content in a treated cell}}{\text{melanine content in a control cell}} - 1 \right) \times 100$$

The results are shown in Table 2 below, wherein the respective compound numbers are keyed to those used in Table 1.

TABLE 2

| Compound No. | Percent increase in the melanine content | Morphological changes | Growth inhibition |
| --- | --- | --- | --- |
| 1 | 427 | ++ | + |
| 2 | 385 | ++ | + |
| 3 | 55 | ++ | + |
| 4 | 64 | ++ | + |
| 5 | 121 | ++ | + |
| 6 | 107 | ++ | + |
| 7 | 235 | ++ | + |
| 8 | 78 | ++ | ± |

TABLE 2-continued

| Compound No. | Percent increase in the melanine content | Morphological changes | Growth inhibition |
| --- | --- | --- | --- |
| 9 | 84 | ++ | ± |

EXAMPLE 2

Male 5-week-old $CDF_1$ mice were used, and $10^6$ Cloudman S-91 melanoma cells were implanted subcutaneously in the inguinal region of each mouse. The following experiments were then conducted.

(A) Twenty-four hours after the transplantation, the first group of mice were administered orally 200 mg/kg body weight of compound 1 dissolved or suspended in a 0.2% aqueous carboxymethyl cellulose solution, and the administration was made once a day and continued for 19 days. The second group of mice were likewise treated with compound 2. The control group was administered 0.1 ml/10 g body weight of carboxymethyl cellulose solution. Twenty-four hours after the final administration, the tumor was removed, its weight was measured and the percent inhibition of tumor growth was determined by comparing the average tumor weight of the treated group with that of the control group. Each group consisted of ten mice. The results are shown in Table 3.

TABLE 3

| Compound No. | Tumor weight (mg) (av. ± standard error) | Percent inhibition |
| --- | --- | --- |
| Control | 1342 ± 355 | — |
| 1 | 199 ± 69 | 85.2 |
| 2 | 352 ± 98 | 73.8 |

(B) Thirteen days after the transplantation, the size of the tumor in each mouse was examined by palpation, and the mice were grouped into three groups on the basis of tumor size so that the groups were as similar as possible. Each group was administered compounds 1, 2 and a vehicle free from the compound respectively, once a day as in (A), and the administration was continued for 7 days. Twenty-four hours after the final administration, the tissue with a tumor was removed, its weight was measured, and the percent inhibition of tumor growth was determined by comparing the average tumor weight of the treated group with that of the control group. Each group consisted of ten mice. The results are shown in Table 4.

TABLE 4

| Compound No. | Tumor weight (mg) (av. ± standard error) | Percent inhibition |
| --- | --- | --- |
| Control | 3259 ± 687 | — |
| 1 | 2120 ± 377 | 34.9 |
| 2 | 1913 ± 359 | 41.3 |

EXAMPLE 3

Experiments were conducted with human neuroblastoma cells (IMR-32) by the procedures described in (1) "Preparation of cell suspensions", (2) "Cell culture and addition of test compounds" and (3) "The growth of cells" for Example 1, except that the culture medium consisted of 90% Ham's F-12 and 10% fatal bovine serum.

Ten days after the transplantation, the effectiveness of the test compounds was rated (+) if under microscopic observation; few cells overlapped each other, giving an image that indicated the contact inhibition of cell growth. The results are shown in Table 5.

TABLE 5

| Compound No. | Effectiveness |
|---|---|
| 1 | + |
| 2 | + |

EXAMPLE 4

Experiments were conducted with human stomach cancer cells (HG-II) as in Example 3 and the results are shown in Table 6. The effectiveness of compounds 1 and 2 was checked on the 14th day after the inoculation.

TABLE 6

| Compound No. | Effectiveness |
|---|---|
| 1 | + |
| 2 | + |

EXAMPLE 5

The ingredients indicated below were mixed thoroughly.
Compound No. 1 in Table 1: 100 parts
Hydrogenpotassium phosphate: 58.5 parts
Crystalline cellulose: 50 parts
Corn starch: 40 parts
Calcium stearate: 1.5 parts The mixture was stamped by a conventional method into tablets each weighing 250 mg and containing 100 mg of the effective ingredient. The tablets were used to treat transplanted lung cancer.

What is claimed is:

1. A pharmaceutical composition in the form of a tablet, capsule or suppository comprising 10–70% by weight of an anthranyl derivative of the formula

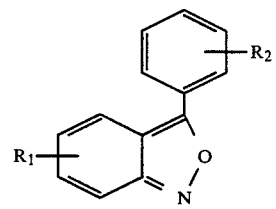

wherein $R_1$ and $R_2$ may be the same or different and represent hydrogen, hydroxyl, lower alkoxy, lower alkyl, nitro or halogen; and a pharmaceutical carrier.

2. A pharmaceutical composition comprising 10–70% by weight of an anthranyl derivative of the formula

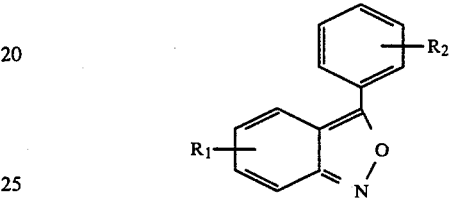

wherein $R_1$ and $R_2$ may be the same or different and represent hydrogen, hydroxyl, lower alkoxy, lower alkyl, nitro or halogen; and a phamaceutical carrier selected from the group consisting of gum arabic powder, saccharose and mannitol.

3. A pharmaceutical composition according to claim 1 wherein the carrier is selected from the group consisting of lactose, starch, mannitol, saccharose, kaolin, crystalline cellulose, talc, calcium carbonate, magnesium stearate, calcium stearate, hydrogenpotassium phosphate, and gum arabic.

4. A composition according to claim 1, wherein $R_1$ is halogen and $R_2$ is hydrogen.

5. A composition according to claim 2, wherein $R_1$ is halogen and $R_2$ is hydrogen.

* * * * *